(12) United States Patent
Skerl et al.

(10) Patent No.: US 12,733,807 B2
(45) Date of Patent: Sep. 15, 2026

(54) MINIATURIZED MEDICAL DEVICE HAVING A WAKE-UP DEVICE

(71) Applicant: BIOTRONIK SE & Co. KG, Berlin (DE)

(72) Inventors: Olaf Skerl, Bad Doberan (DE); André Van Ooyen, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 872 days.

(21) Appl. No.: 17/920,878

(22) PCT Filed: Apr. 26, 2021

(86) PCT No.: PCT/EP2021/060812
§ 371 (c)(1),
(2) Date: Oct. 24, 2022

(87) PCT Pub. No.: WO2021/219537
PCT Pub. Date: Nov. 4, 2021

(65) Prior Publication Data

US 2023/0181040 A1 Jun. 15, 2023

(30) Foreign Application Priority Data

Apr. 29, 2020 (EP) .................................... 20172022

(51) Int. Cl.

| | |
|---|---|
| ***A61B 5/00*** | (2006.01) |
| ***A61B 5/07*** | (2006.01) |
| ***H01H 59/00*** | (2006.01) |

(52) U.S. Cl.
CPC ............ *A61B 5/0031* (2013.01); *A61B 5/076* (2013.01); *H01H 59/00* (2013.01); *A61B 5/6867* (2013.01)

(58) Field of Classification Search
CPC ....... A61B 5/686; A61B 5/6867; A61B 5/076; A61B 5/0031; A61B 2017/00345;
(Continued)

(56) References Cited

U.S. PATENT DOCUMENTS

| | | | |
|---|---|---|---|
| 6,580,947 B1 | 6/2003 | Thompson | |
| 2005/0043594 A1* | 2/2005 | Dinsmoor ............. | A61N 1/378 200/61.04 |

(Continued)

OTHER PUBLICATIONS

Wang, Minfeng, "Resonance-based Addressing in Laminate MEMS Devices", 2012, Electronic Components and Technology Conference, IEEE 62nd IEEE, May 29, 2012, pp. 2048-2052, XP032210875 (Year: 2012).*

(Continued)

*Primary Examiner* — Philip E Stimpert
(74) *Attorney, Agent, or Firm* — Buchanan Ingersoll & Rooney PC

(57) ABSTRACT

A miniaturized medical device comprises an electronic functional device for performing a function of said miniaturized medical device. The miniaturized medical device further comprises a wake-up device for transferring said functional device from a switched-off state to an operational state. Herein, the wake-up device comprises an electrical detection circuit configured to generate a wake-up signal and a switch device. The switch device comprises a switch member, a magnet device attached to the switch member and at least one switch contact. The switch member is excitable by a time-varying magnetic field to perform an oscillating movement for acting onto said at least one switch contact to perform a switching action of the switching device in the electrical detection circuit and to in this way generate the wake-up signal.

13 Claims, 3 Drawing Sheets

(58) Field of Classification Search
CPC ..... A61B 2562/028; H01H 2059/0036; H01H 59/00; H01H 59/0009
USPC ........................................................... 604/19
See application file for complete search history.

(56) References Cited

U.S. PATENT DOCUMENTS

| | | | | |
|---|---|---|---|---|
| 2007/0018762 | A1 | 1/2007 | Wheeler et al. | |
| 2009/0163980 | A1 | 6/2009 | Stevenson | |
| 2017/0126263 | A1 * | 5/2017 | Rinaldi | H10N 30/40 |
| 2018/0161576 | A1 | 6/2018 | Ostroff et al. | |

OTHER PUBLICATIONS

International Search Report (PCT/ISA/210) and Written Opinion (PCT/ISA/237) mailed on Jul. 28, 2021, by the European Patent Office as the International Searching Authority for International Application No. PCT/EP2021/060812.

Wang, et al., “Resonance-based addressing in laminate MEMS devices”, Electronic Components and Technology Conference ( ECTC). 2012 IEEE 62nd, IEEE, May 29, 2012 (May 29, 2012), pp. 2048-2052, XP032210875.

* cited by examiner

MINIATURIZED MEDICAL DEVICE HAVING A WAKE-UP DEVICE

CROSS-REFERENCE TO RELATED APPLICATIONS

This application is the United States National Phase under 35 U.S.C. § 371 of PCT International Patent Application No. PCT/EP2021/060812, filed on Apr. 26, 2021, which claims the benefit of European Patent Application No. 20172022.4, filed on Apr. 29, 2020, the disclosures of which are hereby incorporated by reference herein in their entireties.

TECHNICAL FIELD

The present invention concerns a miniaturized medical device according to the preamble of claim 1.

BACKGROUND

Such miniaturized medical device (in short MMG) comprises a functional device in the shape of an electronics or electronic module for performing a function of the miniaturized medical device, the functional device having an operational state for performing the function and a switched-off state. A wake-up device serves to transfer the functional device from the switched-off state to the operational state in order to execute the predetermined function in the operational state.

Such a miniaturized medical device may, in particular, be implantable into a patient.

Such a miniaturized medical device may, for example, be a sensing system that can be implanted in a patient's vessel, for example, to measure a parameter such as a blood pressure or a blood flow within the vessel. The sensing system can be used to monitor a patient's condition, for example, for observing and diagnosing a course of disease, wherein the miniaturized medical device may be designed to communicate with an external device (located outside the patient) to transmit the measurement results to the external device after measurement by the miniaturized medical device.

Alternatively, such a miniaturized medical device may be designed as an implantable stimulation device, for example, with a pacemaker or neuro-stimulation function, or alternatively a diagnostic device, such as a diagnostic patch, or a wearable device.

A miniaturized medical device comprises a functional device in the form of an electronics unit or electronic module, which is formed, for example, by a processor and serves to to perform a function in an active operational state of the medical device, for example, a measurement function to measure a parameter of a patient, for example, a blood pressure. To operate the functional device, the miniaturized medical device comprises an energy storage element, particularly in the form of an electric battery, which feeds the functional device and supplies it with power in its operational state.

An implantable medical device should usually remain in a patient after implantation for a long period of time, for example, several years, which requires that the energy storage has a corresponding capacity to supply the functional equipment. However, because such a medical device should, for example, have a small shape in order to be able to implant the medical device into small blood vessels, for example, an artery or the like, the available space for the energy storage element and thus also the capacity of a battery realizing the energy storage is limited.

From the desire to miniaturize a battery for use in miniaturized medical devices it follows that the power consumption of the medical device should be low. For this it is desirable that the medical device is not permanently active, but is only switched to an active operational state (in which the functional device can perform a predetermined function, for example, to measure a patient's parameter) if required, but otherwise the miniaturized medical device is largely inactive and therefore consumes no or at least only very little power in passive phases. For this purpose, the functional device of the miniaturized medical device is preferably in the switched-off state for most of the time and can be transferred from the switched-off state to the operational state by the wake-up device in order to then carry out a predetermined function in the operational state. After executing the function, the functional device may switch back to the switched-off state until the functional device is woken up again by the wake-up device and thus is transferred to the operational state.

Herein the wish exists to be able to wake up the functional device flexibly in order to be able to switch on the functional device in a user-triggered manner. This should come at a low power consumption.

An implantable neuro-stimulation system known from U.S. Publication No. 2018/0161576 A1 comprises a GMR sensor designed to detect the presence of a magnetic field. By detecting a magnetic field, the system can be switched on so that a stimulation function can be performed.

U.S. Publication No. 2009/0163980 A1 describes an MRI-compatible electronic medical therapy system for temporarily preventing current flow through an implanted lead wire in the presence of an induced radiofrequency, magnetic, or static field. One or more normally closed switches are disposed in series between the device and one or more distal electrodes.

U.S. Pat. No. 6,580,947 B1 describes an implantable medical device using a solid state sensor for detecting an external magnetic field, the sensor comprising a magnetic field responsive microelectromechanical (MEM) switch. A beam of the switch carries a ferromagnetic layer, such that the beam may be deflected by a static magnetic field in order to close the switch.

There is a desire to be able to wake up a miniaturized medical device in a contactless fashion, in particular, when the miniaturized medical device is implanted in a patient. Herein, a waking up of the device shall be possible also when the device is implanted deeply in a patient, wherein a current flow in an inactive state of the device, i.e., in the switched-off state of the functional device, shall be limited, preferably zero.

The present disclosure is directed toward overcoming one or more of the above-mentioned problems, though not necessarily limited to embodiments that do.

SUMMARY

It is an objective of the instant invention to provide a miniaturized medical device as well as a system and a method that enable energy-efficient operation of the miniaturized medical device, while allowing a reliable wake up even when the device is deeply implanted in a patient.

At least this objective is achieved by a miniaturized medical device comprising the features of claim 1.

Accordingly, the wake-up device comprises an electrical detection circuit configured to generate a wake-up signal for waking up said functional device and a switch device arranged in the electrical detection circuit, the switch device comprising a switch member, a magnet device attached to the switch member and at least one switch contact associated with the electrical detection circuit. The switch member is excitable by a time-varying magnetic field to perform an oscillating movement. The switch member is configured, caused by said oscillating movement, to act onto said at least one switch contact to perform a switching action of the switch device in the electrical detection circuit for generating the wake-up signal.

Accordingly, a switch device arranged in an electrical detection circuit is used to generate a wake-up signal. The switch device may, for example, be fabricated as a micro-electromechanical (MEMS) switch and comprises a switch member, for example, in the shape of a cantilever, which is excitable to act onto a switch contact for switching the switching device.

Herein, the switch member is excitable by means of a time-varying magnetic field. The switch member hence may perform an oscillating movement, the oscillating movement causing, e.g., an oscillating action on the switch contact, which may be detected by means of the electrical detection circuit.

MEMS elements generally are integrated into a chip and are fabricated, for example, within a substrate, for example, made from silicon. Accordingly, the switch member, preferably in the shape of a cantilever beam, is fabricated within the chip, wherein the switch member is deflectable and may perform an oscillating movement upon excitation by means of an external time-varying magnetic field.

In one embodiment, the switch member forms a mechanical resonant system having a resonant frequency, wherein the switch member is excitable by a time-varying magnetic field to perform an oscillating movement at the resonant frequency. Upon an external impulse excitation, the switch member generally tends to oscillate at its resonant frequency. An excitation by a time-varying magnetic field herein causes the switch member to perform a forced oscillation, wherein the excitation is strongest if the excitation takes place at the resonant frequency of the switch member. Hence, generally an excitation of the switch member shall take place at its mechanical resonant frequency, allowing for an efficient excitation in that an excitation at a small magnetic field amplitude may cause an oscillation of the switch member at a substantial mechanical oscillation amplitude.

The resonant frequency of the switch member may, for example, lie in between 10 kHz and 30 kHz, for example, at 20 kHz.

Due to the excitation of the switch member at its resonant frequency, a time-varying magnetic field of small field strength, for example, smaller than 100 μT (referring to the location of the miniaturized medical device), may be sufficient to excite the switch member to oscillate. This allows for an efficient and reliable wake-up action even for a medical device which is deeply implanted into a patient, or through clothes.

By exciting the switch member a switching action of the switching device is caused. In particular, by the movement of the switching member the switch device may be transferred cyclically into a closed state, such that a current flows only when an actual excitation of the switch member takes place. This allows for a small, preferably zero current flow in the switched-off state of the functional device, such that energy consumption is effectively reduced to a minimum when the medical device is inactive.

In one embodiment, the switch device comprises a contact element arranged on the switch member, the contact element being configured to establish an electrical contact with the at least one switch contact. The contact element arranged on the switch member is electrically conductive, and so is the switch contact arranged, for example, on a substrate of the switch device. By deflecting the switch member, the contact element arranged on the switch member may come into electrical contact with the switch contact, such that an electrical connection is established. Due to the oscillating movement of the switch member, herein, the electrical contact may be established in a cyclical manner, such that the switch device oscillates between an opened state and a closed state due to the oscillating movement of the switch member.

A magnet device is connected to the switch member in order to allow for an interaction of the switch member with the external time-varying magnetic field. The magnet device may be a passive member, such as a ferromagnetic element, for example, in the shape of a ferromagnetic layer formed on the switch member. Alternatively, the magnet device may be an active device in the shape of a permanent magnet, arranged, for example, at a head of the switch member and hence allowing for a magnetic interaction of the switch member with the external time-varying magnetic field.

In one embodiment, the switch device comprises a substrate, the switch member being formed as a cantilever which is integrally connected to the substrate and is movable with respect to the substrate upon excitation by the time-varying magnetic field. The switch member, in one embodiment, may, for example, be connected at one end to the substrate and may be free to oscillate at a head opposite the connected end. The contact element herein may be arranged on the head, such that by a movement of the head an electrical contact may be established in order to perform a switching action of the switch device.

The oscillating movement of the switch member is detected by means of the electrical detection circuit, the electrical detection circuit being configured to generate the wake-up signal causing the functional device to be transferred from its switched-off state to the operational state. The electrical detection circuit may be configured to detect a closing of the switch device, wherein a single closing of the switch device—e.g., by establishing a contact between the contact element arranged on the switch member and the switch contact of the switch device—may be sufficient to cause a generation of the wake-up signal.

In one embodiment, when excited by the external time-varying magnetic field, the oscillating movement of the switch member causes a cyclical closing of the switch device, which causes the generation of the wake-up signal by means of the electrical detection circuit. For this, the electrical detection circuit may, for example, comprise an energy storage element for storing electrical energy, the energy storage element being chargeable by said switching action of the switching device. Upon the cyclic movement of the switch member and due to the cyclical closing of the switch device, hence, the energy storage element is cyclically charged, such that a charge within the energy storage element cyclically builds up, which can be detected by suitable means of the electrical detection circuit.

Preferably, the switch member is designed to perform an oscillating movement, when excited by an external time-varying magnetic field, with an increasing amplitude over the time, until a closing of the switch device is achieved. In other word, the switch member may perform a number of up and down movements with an increasing amplitude over the time, until the deflection of the switch member is sufficient to establish a physical and electrical contact between the contact element an the at least one switch contact.

In particular, it can be detected if the charge of the energy storage element has built up to exceed a predefined threshold, and if this is the case, the wake-up signal may be generated.

The energy storage element may, for example, have the shape of a capacitor. By cyclically closing the switch, hence, current pulses may be caused to cyclically flow into the capacitor, such that a charge of the capacitor cyclically builds up.

The capacitor may, for example, have a capacitance larger than 1 nF, for example, 2 nF.

In one embodiment, the electrical detection circuit comprises a comparator device to assess a charging state of the energy storage element. The comparator device is connected to the energy storage element and compares a voltage at the energy storage element, for example, in the shape of a capacitor, to a predefined reference voltage functioning as a threshold. If the voltage at the energy storage element is found to exceed the reference voltage, an output signal is generated by the comparator device, the output signal preferably representing the wake-up signal causing to wake up the functional device.

In one embodiment, the electrical detection circuit comprises a resistor which is connected in parallel to the energy storage element. The resistor causes the energy storage element to (slowly) discharge, such that the charge of the energy storage element is reduced over time at a time constant substantially larger than a periodicity of the cyclic charging of the energy storage element. Such discharging may counteract a charging of the energy storage element due to a switching of the switching device which is not due to an external excitation by means of a suitable activator device, but due to an accidental movement of the switch member, for example, due to a patient's body movement.

The resistor may, for example, have a rather high resistance, for example, larger than 1 MΩ, for example, 10 MΩ.

A system may comprise a miniaturized medical device of the type described above and an activator device configured to generate a time-varying magnetic field for exciting the switch member. Whereas the miniaturized medical device may be implantable into a patient, the activator device acts outside of the patient and is configured to excite a switching action of the switch device in a contactless fashion.

The activator device may, for example, comprise an alternating current source and an electrical coil for generating the time-varying magnetic field.

The activator device may be configured to generate a magnetic field at variant frequencies, for example, in a range of frequencies which includes the nominal resonant frequency of the switch member. If, for example, the switch member has a nominal resonant frequency of 20 kHz, the activator device may be configured to generate a magnetic field, for example, in a frequency sweep, in between 15 kHz and 25 kHz. In this way an effective excitation of the switch member can be ensured, wherein mechanical tolerances of the switch member and corresponding deviations from the nominal resonant frequency are counteracted by generating an excitation field in a rather broad frequency range.

An objective is also achieved by a method for operating a miniaturized medical device, the method comprising: providing an electronic functional device for performing a function of said miniaturized medical device, said functional device having an operational state for performing said function and a switched-off state; providing a wake-up device for transferring said functional device from said switched-off state to said operational state; and generating a wake-up signal for waking up said functional device using an electrical detection circuit of the wake-up device and a switch device arranged in the electrical detection circuit, the switch device comprising a switch member, a magnet device attached to the switch member and at least one switch contact associated with the electrical detection circuit; wherein the generating of the wake-up signal includes exciting the switch member by a time-varying magnetic field to perform an oscillating movement, wherein the switch member, caused by said oscillating movement, acts onto said at least one switch contact to perform a switching action of the switching device in the electrical detection circuit for generating the wake-up signal. Preferably, the oscillating movement propagates or continues with an increasing amplitude over the time of the excitation by the time varying magnetic field.

The advantages and advantageous embodiments described above for the miniaturized medical device and the system equally apply also to the method, such that it shall be referred to the above.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The idea(s) behind the present invention shall subsequently be explained in more detail by referring to the embodiments shown in the figures. Herein.

DETAILED DESCRIPTION

Figure 1:
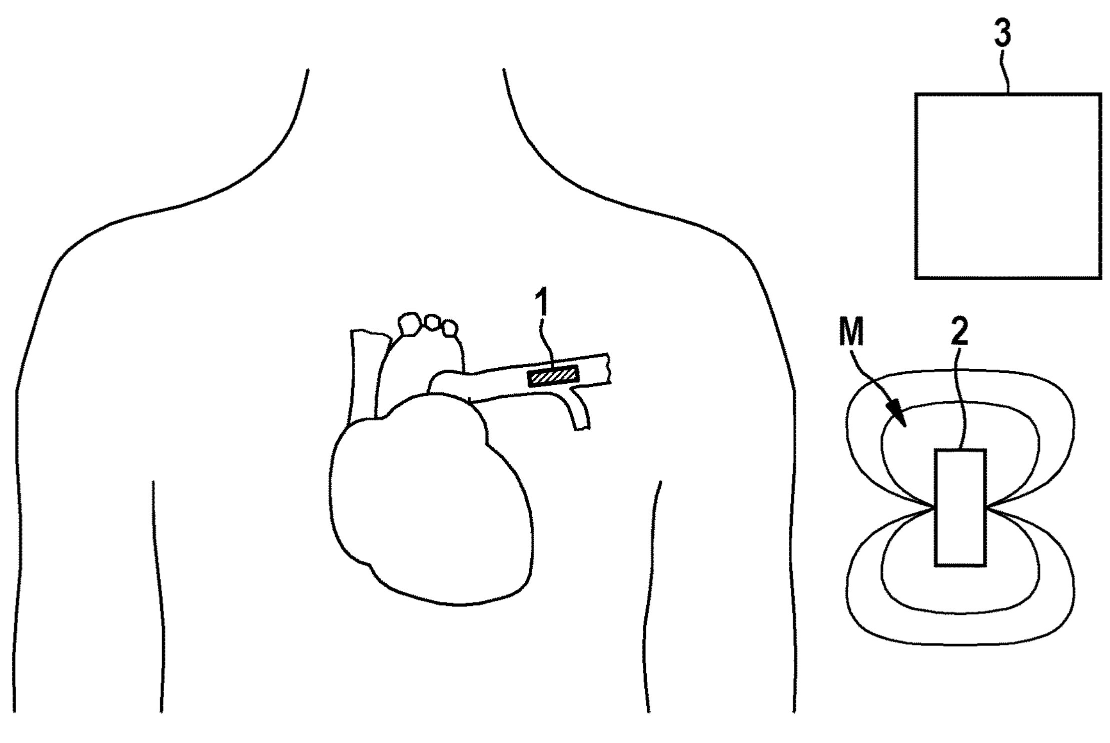
FIG. 1 shows a schematic view of a medical device implanted in a patient, along with an external signal source and an external monitoring device.

FIG. 1 shows a schematic view of an embodiment of a miniaturized medical device 1, which may be configured, for example, as a sensing system for measuring a parameter of a patient, for example, blood pressure, and is implanted in a vessel, for example, an artery, of the patient.

The medical device 1 is used to perform a function in a patient over a prolonged period of time, such as a measurement function or a cardiac or neuronal stimulation function for the purpose of therapy. For example, the medical device 1 shall remain in a patient for multiple years in order to record measurement data during the lifetime of the medical device 1 and to communicate with an external device 3, so that the measurement data may be used to diagnose or monitor the condition of the patient.

Figure 2:
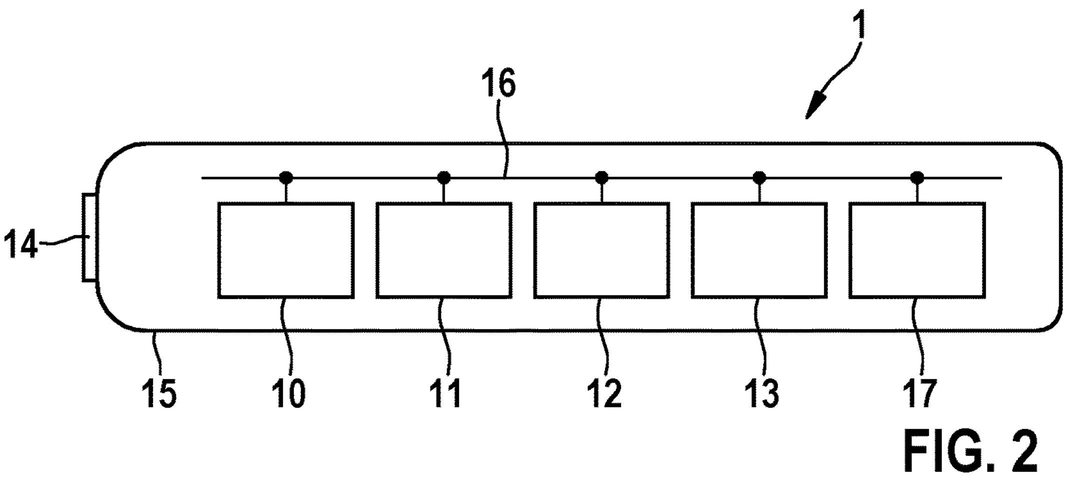
FIG. 2 shows a schematic view of a miniaturized medical device.

Such a medical device 1 should be small in size. As schematically shown in FIG. 2, the medical device 1, for example, comprises a housing 15, which, in one embodiment, may comprise an essentially cylindrical or rectangular, preferably with rounded edges, housing shape, with a length between 10 mm and 40 mm and a diameter, for example, between 3 mm and 10 mm, wherein other dimensions are also conceivable and possible.

Such a medical device 1 comprises, in the example of the shown embodiment, an electronic functional device 10 which is formed, for example, by a processor and serves to perform a predetermined function, for example, a measuring function or a therapy function. The medical device 1 in addition comprises a memory 11, e.g., in the form of a RAM (Random Access Memory), a wake-up device 12, an energy storage 13, for example, in the form of a battery, and a communication device 17 for communicating with an external device 3. The different functional units are encapsulated together in the housing 15 in a fluid-tight manner and are interconnected, for example, by a bus system 16 for a data exchange in between the different devices.

The medical device 1 in addition, in the shown embodiment, comprises, for example, a measurement sensor 14, which is used together with the functional device 10 to perform a measurement in order to record measurement data, for example, to measure a pressure within a patient's vessel. A measurement may be performed over a predetermined period of time, for example, a few seconds or a few minutes, with measurement data being stored, e.g., temporarily in the memory 11 during a measurement and communicated to the external device 3 via the communication device 17.

Because the medical device 1 has small dimensions, the size of the energy storage 13 is also necessarily limited. Because the medical device 1 is to remain in a patient and be operative for a prolonged period of time, for example, several years, it is desired that the medical device 1 operates energy-efficiently, thus requiring little power, but still functions reliably to perform one or more predetermined functions.

In order to reduce the energy consumption of the medical device 1, in the embodiment of FIG. 2 the functional device 10 does not operate continuously and at all times, but is only switched from a switched-off state to an operational state when required in order to carry out a function in the operational state. In the switched-off state the functional device 10 is shut down and causes no or only a very limited power consumption, so that in the switched-off state of the functional device 10 the system of the medical device 1 exhibits a low overall power consumption.

In order to transfer the functional device 10 from the switched-off state to the operational state, the wake-up device 12 is provided, which serves to switch on the functional device 10 based on a signal provided from an external activator device 2 (see FIG. 1).

Figure 3:
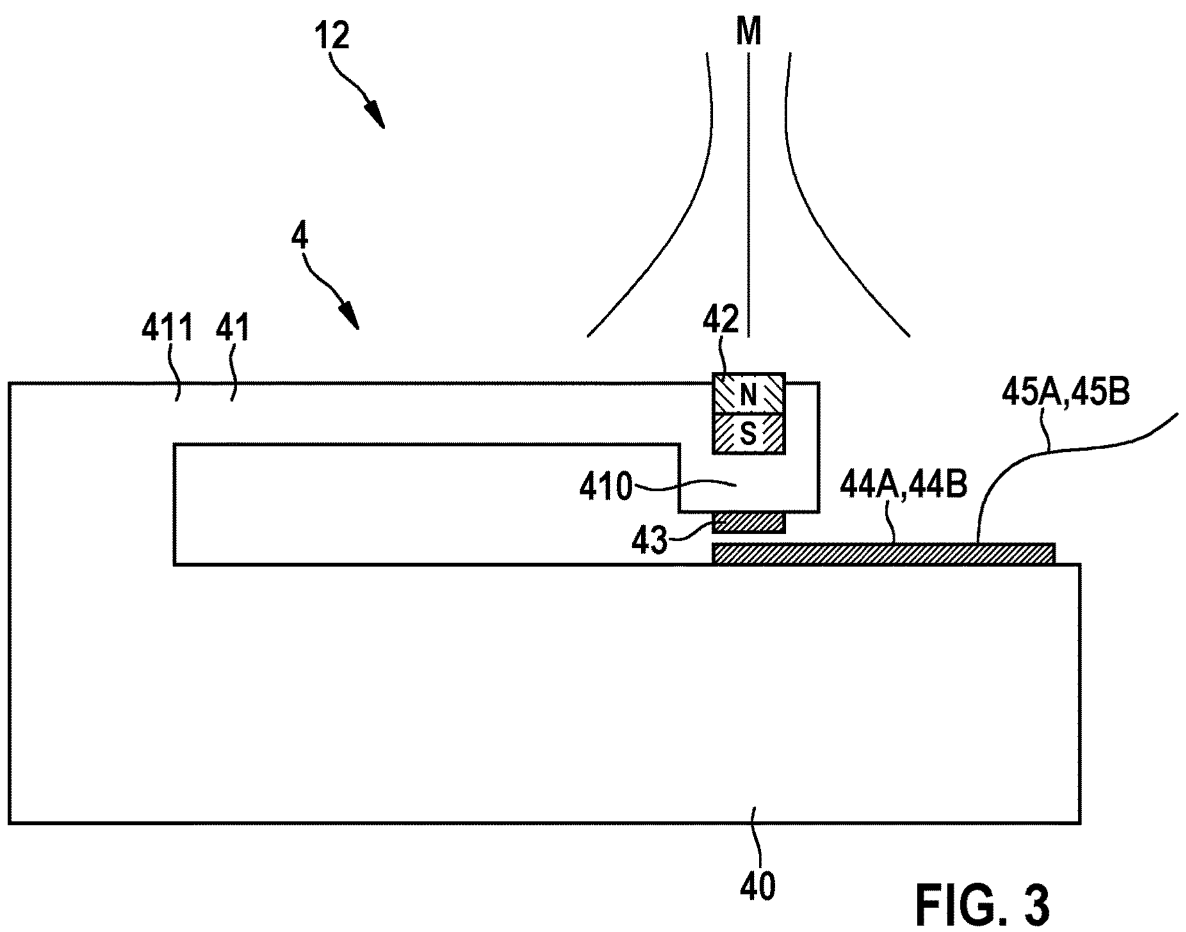
FIG. 3 shows a drawing of an embodiment of a switch device of a wake-up device of the miniaturized medical device.

Referring now to FIG. 3, the wake-up device 12 comprises a switch device 4 which is fabricated as a MEMS switch from a substrate 40, for example, a silicon substrate, on which a switch member 41 in the shape of a cantilever is formed.

The switch member 41 at one end 411 is connected to the substrate 40 and, with a head 410 opposite the connected end 411, is movable with respect to the substrate 40. At a face facing the substrate 40, herein, a contact element 43 is arranged on the head 410, the contact element 43 being associated with a pair of switch contacts 44A, 44B arranged on the substrate 40 facing the head 410.

Figure 4:
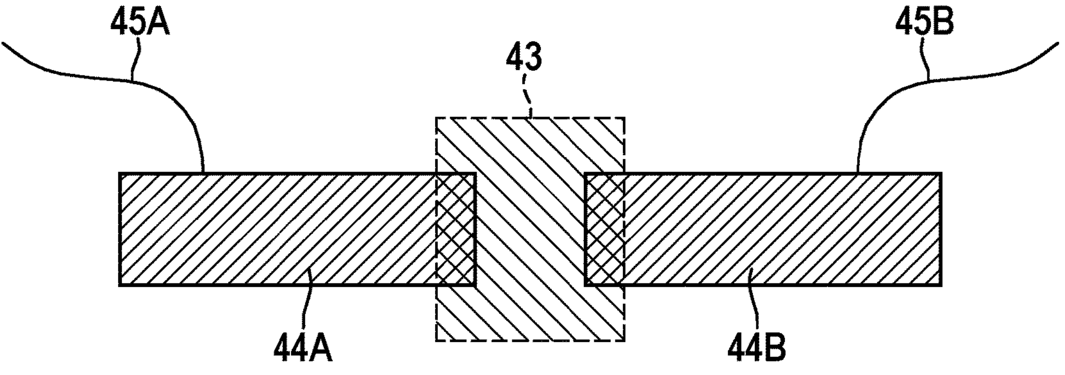
FIG. 4 shows a schematic drawing of a contact element of a switch member of the switch device and of switch contacts to be contacted by the contact element.

As visible from FIG. 4, the contact element 43 arranged on the head 410 of the switch member 41 may, for example, be configured as a bridging element which may electrically bridge the switch contacts 44A, 44B in an electrically contacting state in which the contact element 43 is in electrical contact with both switch contacts 44A, 44B, such that a current may flow in between the switch contacts 44A, 44B.

Connection lines 45A, 45B are electrically connected to the switch contacts 44A, 44B to connect the switch device 4 to an electrical detection circuit 123, as shall subsequently be described with reference to FIG. 5.

Referring again to FIG. 3, a magnet device 42 in the shape of a permanent magnet having magnet poles N, S is arranged on the head 410, the magnet device 42 serving to interact to with an external time-varying magnetic field M to cause a deflection of the switch member 41.

The switch member 41, in one embodiment, forms a mechanical resonant system having a nominal resonant frequency, for example, in between 10 kHz and 30 kHz, for example, at 20 kHz. Using an external time-varying magnetic field M at or at least close to the resonant frequency of the switch member 41, the switch member 41 hence may be excited to perform an oscillating movement, in the course of which the contact element 43 arranged on the head 410 of the switch member 41 cyclically comes into electrical contact with the switch contacts 44A, 44B, such that the switch contacts 44A, 44B are cyclically bridged and the switch device 4 hence is cyclically closed. Particularly, the switch member 41, the magnetic device 42 and the external time-varying magnetic field M are designed such that the oscillating movement increases in terms of the amplitude until after several oscillating movements a physical and electric contact between the contact element 43 and the switch contacts 44A, 44B is established.

Figure 5:
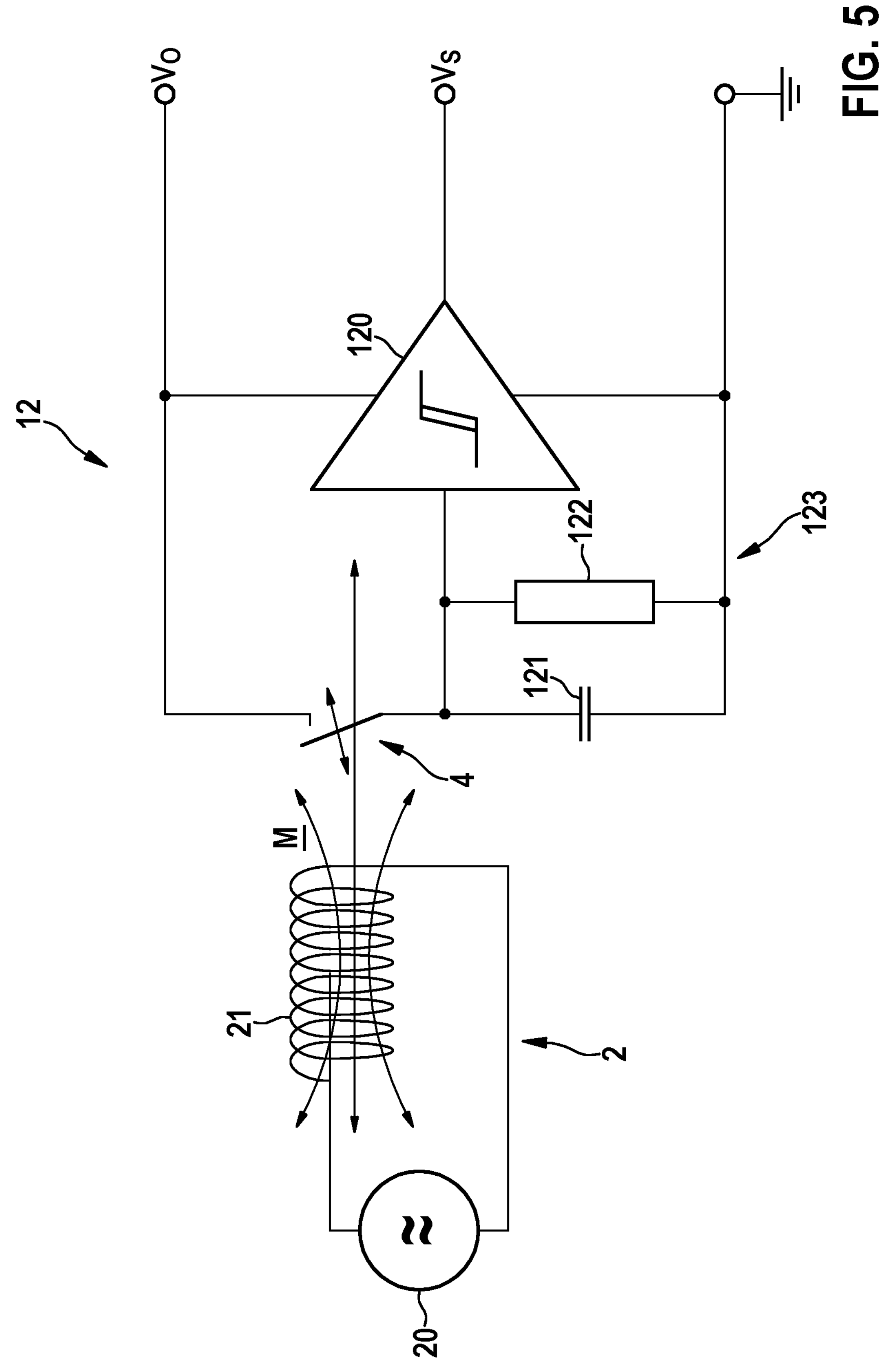
FIG. 5 shows a schematic drawing of the switch device in an electrical detection circuit, upon excitation by means of an external time-varying magnetic field caused by an activator device.

Referring now to FIG. 5, the switch device 4 is part of an electrical detection circuit 123 which serves to detect a cyclical closing of the switch device 4 due to an external time-varying magnetic field M causing an oscillation of the switch member 41. The electrical detection circuit 123 comprises an energy storage element 121 in the shape of a capacitor connected in between a ground potential and an input of a comparator device 120, a resistor 122 being connected in parallel to the energy storage element 121. The switch device 4 is arranged in between the energy storage element 121 and the potential of a supply voltage V0, such that by closing the switch device 4 the energy storage element 121 cyclically is connected to the supply voltage V0.

The switching of the switch device 4 is caused by an activator device 2 which is external to the patient and interacts with the wake-up device 12 in a contactless fashion. The activator device 2 comprises an alternating current source 20 and a magnetic excitation coil 21, the activator device 2 being configured to generate a time-varying magnetic field M by feeding an alternating current through the coil 21.

The activator device 2 may, in particular, be configured to generate a magnetic field M at the resonant frequency of the switch member 41 of the switch device 4. Herein, to avoid effects of tolerances in the mechanical construction of the switch member 41 and corresponding deviations of the actual resonant frequency of the switch member 41 from its nominal resonant frequency, the activator device 2 may be configured to generate, for example, in a frequency sweep, a frequency-variable magnetic field M in a frequency range encompassing the nominal resonant frequency of the switch member 41.

If, for example, the switch member 41 comprises a nominal resonant frequency of 20 kHz, the activator device 2 may be configured to generate a time-varying magnetic field M in a frequency range in between and 15 kHz and 25 kHz.

Due to the excitation of the switch member 41 at or close to its nominal resonant frequency, the switch member 41 is caused to oscillate. The contact element 43 hence cyclically comes into contact with the switch contacts 44A, 44B, and hence connects the supply voltage V0 to the energy storage element 121 in the shape of the capacitor. The energy storage element 121 hence is cyclically charged by means of current pulses caused by the cyclical switching of the switch device 4, wherein the charge builds up over time by the cyclical closing of the switch device 4 such that the voltage across the energy storage element 121 increases.

This may be detected by means of the comparator device 120, which may switch to a high-level once the voltage of the energy storage element 121 exceeds a predefined reference voltage, such that in this case an output signal VS is generated representing a wake-up signal for waking up the functional device 10 of the medical device 1.

The resistor 122 serves to discharge the energy storage element 121 in the shape of the capacitor. The resistor 122 may have a rather large resistance value, for example, larger than 1 MΩ, such that a discharging of the energy storage element 121 takes place slowly. The resistor 122, in particular, serves to avoid that an accidental charging of the energy storage element 121, for example, by a switching of the switch device 4 due to, e.g., a patient's movement, may lead to a wake-up signal.

Because the switch member 41 of the switch device 4 is excited by a time-varying magnetic field M at or at least close to the resonant frequency of the switch member 41, an oscillating deflection of the switch member 41 may be caused already at low magnetic field strengths, for example, smaller than 100 μT, for example, 1 μT (referring to the is location of the switch device 4). This makes it possible to reliably wake up a medical device 1 which is deeply implanted in a patient, using an activator device 2 of simple and light built and construction.

Because a current only flows into the energy storage element 121 if the switch device 4 is closed on the occurrence of the external magnetic field M, the wake-up device 12 exhibits low power consumption at effectively zero current in a phase in which no external magnetic field M is present. The comparator device 120 herein may be a so called Schmitt Trigger, which allows for an energy-efficient operation with negligible current flow.

The present invention is not limited to the embodiments described above, but may be implemented in a different fashion.

Due to the fabrication of the switch device having a switch member formed as a cantilever in the MEMS technology, a simple and easy manufacturing of the switch device may be possible.

Due to the operation at the resonant frequency of the switch member, an energy efficient excitation at low field strengths becomes possible, hence allowing for an efficient and reliable wake up function.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Miniaturized medical device
10 Functional device
11 Memory device
12 Wake-up device
120 Comparator device
121 Energy storage element (capacitor)
122 Resistor
123 Electrical detection circuit
13 Energy storage
14 Sensor device
15 Housing
16 Bus system
17 Communication device
2 Activator device
20 Alternating current source
21 Coil
3 External device
4 Switch device
40 Substrate
41 Switch member (cantilever)
410 Head
411 End
42 Magnet device
43 Contact element
44A, 44B Switch contacts
45A, 45B Connection lines
M Magnetic field
N, S Magnet poles
V0 Supply voltage
VS Output signal

The invention claimed is:

1. A miniaturized medical device, comprising: an electronic functional device for performing a function of said miniaturized medical device, said functional device having an operational state for performing said function and a switched-off state, and a wake-up device for transferring said functional device from said switched-off state to said operational state, wherein the wake-up device comprises an electrical detection circuit configured to generate a wake-up signal for waking up said functional device and a switch device arranged in the electrical detection circuit, the switch device comprising a switch member, a magnet device, wherein the magnet device is connected to or attached to the switch member, and a contact element attached to the switch member and at least one switch contact associated with the electrical detection circuit, wherein the switch member is excitable by a time-varying magnetic field to perform an oscillating movement, wherein the switch member forms a mechanical resonant system having a resonant frequency and is configured, caused by oscillating movement corresponding to the resonant frequency, to cause the contact element to cycle between contact and non-contact with said at least one switch contact to perform a switching action of the switching device in the electrical detection circuit for generating the wake-up signal, wherein the magnet device oscillates with the switch member.

2. The miniaturized medical device according to claim 1, wherein the switch device is a MEMS switch.

3. The miniaturized medical device according to claim 1, wherein the magnet device is a permanent magnet.

4. The miniaturized medical device according to claim 1, wherein the switch device comprises a substrate, wherein the switch member is formed as a cantilever which is movable with respect to the substrate upon excitation by said time-varying magnetic field.

5. The miniaturized medical device according to claim 1, wherein the electrical detection circuit comprises an energy storage element for storing electrical energy, the energy storage element being chargeable by said switching action of the switching device.

6. The miniaturized medical device according to claim 5, wherein the energy storage element is a capacitor.

7. The miniaturized medical device according to claim 5, wherein the switch device is configured, by the oscillating movement corresponding to the resonant frequency of the switch member, to cyclically charge the energy storage element.

8. The miniaturized medical device according to claim 5, wherein the electrical detection circuit comprises a comparator device to assess a charging state of said energy storage element.

9. The miniaturized medical device according to claim 8, wherein the comparator device is configured to generate said wake-up signal.

10. The miniaturized medical device according to claim 5, wherein the electrical detection circuit comprises a resistor connected electrically in parallel to the energy storage element.

11. System, comprising a miniaturized medical device according to claim 1 and an activator device configured to generate said time-varying magnetic field.

12. The system according to claim 11, wherein the activator device is configured to generate said time-varying magnetic field at the resonant frequency of the switch member.

13. A method for operating a miniaturized medical device, comprising: providing an electronic functional device for performing a function of said miniaturized medical device, said functional device having an operational state for performing said function and a switched-off state; and providing a wake-up device for transferring said functional device from said switched-off state to said operational state, wherein generating a wake-up signal for waking up said functional device using an electrical detection circuit of the wake-up device and a switch device arranged in the electrical detection circuit, the switch device comprising a switch member, a magnet device, wherein the magnet device is connected to or attached to the switch member, and a contact element attached to the switch member and at least one switch contact associated with the electrical detection circuit; wherein the generating of the wake-up signal includes exciting the switch member by a time-varying magnetic field to perform an oscillating movement, wherein the switch member is a mechanical resonant system having a resonant frequency and, due to oscillating movement corresponding to the resonant frequency, causes the contact element to cycle between contact and non-contact with said at least one switch contact to perform a switching action of the switching device in the electrical detection circuit for generating the wake-up signal, wherein the magnet device oscillates with the switch member.

* * * * *